United States Patent [19] [11] 4,095,970
MacDonald [45] Jun. 20, 1978

[54] 2,6-DICHLOROTHIOLBENZOATES AND USE THEREOF AS PLANT GROWTH REGULATORS

[75] Inventor: Alan A. MacDonald, Albany, Calif.

[73] Assignee: Stauffer Chemical Company, Westport, Conn.

[21] Appl. No.: 696,672

[22] Filed: Jun. 16, 1976

[51] Int. Cl.² .................. A01N 9/12; C07C 153/09
[52] U.S. Cl. .................... 71/72; 260/455 R; 71/100; 71/76
[58] Field of Search .............. 260/455 R; 71/100

[56] References Cited
U.S. PATENT DOCUMENTS 3,282,977  11/1966  Barnas ........................ 260/455 R
3,296,292   1/1967  Richter et al. ............... 260/455 R

FOREIGN PATENT DOCUMENTS 1,146,692  2/1966  United Kingdom ............ 260/455 R Primary Examiner—Delbert R. Phillips
Attorney, Agent, or Firm—Daniel C. Block

[57] ABSTRACT

Novel compounds of the formula

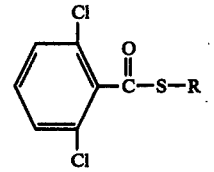

wherein R is lower alkyl, cycloalkyl, cycloalkylmethyl, aryl, or aralkyl are useful as plant growth regulators.

52 Claims, No Drawings

2,6-DICHLOROTHIOLBENZOATES AND USE THEREOF AS PLANT GROWTH REGULATORS

This invention relates to novel 2,6-dichlorothiolbenzoates, to the use thereof as plant growth regulators, and to plant growth regulatory compositions containing said novel compounds.

The novel compounds of this invention are 2,6-dichlorothiolbenzoates of the general structural formula:

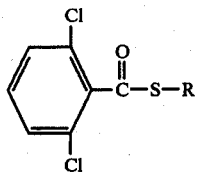

wherein R is selected from the group consisting of lower alkyl, cycloalkyl, cycloalkylmethyl, aryl and aralkyl.

The term "alkyl" is meant to include straight and branched chain alkyl radicals having 1-6 carbon atoms, e.g., methyl, ethyl, n-propyl, i-propyl, n-butyl, i-butyl, sec-butyl, t-butyl, n-pentyl, neopentyl and the like. The term "cycloalkyl" is meant to include cycloalkyl radicals having 3-6 carbon atoms, i.e., cyclopropyl, cyclobutyl, cyclopentyl, and cyclohexyl. The term "aryl" is meant to include phenyl and substituted phenyl radicals, and the term "aralkyl" is meant to include aralkyl radicals having 7-10 carbon atoms, for example benzyl, phenethyl and the like, also substituted derivatives thereof.

The term "plant growth regulator" or variants thereof, and as employed throughout the specification and claims, is used to describe those materials which exhibit certain effects on the growth habits of plants, including, but not limited thereto, dwarfing or stunting, regulation of the onset of flowering and the number of flowers produced, regulation of amount of fruit set, defoliation, reduction or inhibition of lateral growth, and shortening of internodes. Plant growth regulators, for example, may be used as stunting agents on grasses, thus allowing extended periods between grass cutting, while maintaining favorable landscape conditions. On certain crop species, greater pod yield allows increased production.

Each of the compounds of the present invention can be prepared by reacting 2,6-dichlorobenzoyl chloride with the appropriate mercaptan in the presence of a base acceptor, for example a tertiary amine, such as triethyl amine. The reaction perferably takes placed in a suitable solvent at a temperature from about 0° to 150° C. Suitable solvents include organic solvents inert to the reaction, for example, benzene, toluene, carbon tetrachloride, and the like. Excess triethyl amine can be utilized as the solvent, if desired.

The following examples illustrate preparation of typical 2,6-dichlorothiolbenzoates of this invention and evaluation thereof as plant growth regulators.

EXAMPLE I

This example illustrates the preparation of n-propyl-2,6-dichlorothiolbenzoate.

To a 250 ml three-necked, round-bottom flask, equipped with a paddle stirrer, thermometer, condenser, and dropping funnel were added 100 ml triethyl amine as solvent and 7.62 g (0.10 mole) of n-propyl mercaptan. To this was added 21 g (0.10 mole) of 2,6-dichlorobenzoyl chloride at a rate to maintain the temperature at between 30° C and 55° C. After the addition was complete, the reaction mixture was heated at 90° C for about 10 minutes. The resulting viscous slurry was stirred for two hours and then permitted to stand at room temperature for about 12 hours. The solution was then poured into rapidly stirring ice water (600 ml) to separate the product as the liquid lower layer of the resulting mixture. The product was extracted with three 100 ml portions of methylene chloride and the resulting extract washed with 4N-hydrochloric acid to remove the triethyl amine and then with saturated sodium bicarbonate solution to remove excess acid. The product was then washed with two 100 ml portions of water and dried over anhydrous magnesium sulfate. The product was filtered and stripped of volatiles. A yield of 23.5 g (theory = 24.9 g) of a product having an $N_D^{30}$ of 1.5455 was obtained. The structure of the product was confirmed by NMR and IR.

Other compounds of this invention were prepared in an analogous manner from 2,6-dichlorobenzoyl chloride and the appropriate mercaptan. The following is a table of compounds representative of those embodied by the present invention. Compound numbers have been assigned to them and are used for identification throughout the balance of the specification.

TABLE I

| Compound No. | R | Physical Constant m.p. (° C) or $N_D^{30}$ |
|---|---|---|
| 1 | -n-C₃H₇ | 1.5455 |
| 2 | -i-C₃H₇ | 1.5285 |
| 3 | —CH₃ | 72 – 74 |
| 4 | —C₂H₅ | 1.5523 |
| 5 | -n-C₄H₉ | 1.5350 |
| 6 | -i-C₄H₉ | 1.5345 |
| 7 | -sec-C₄H₉ | 1.5345 |
| 8 | -t-C₄H₉ | 1.5308 |
| 9 | —CH₂–cyclopropyl | 1.5350 |
| 10 | —CH₂C(CH₃)₃ | 1.5284 |
| 11 | -(2-thienyl) | 82 – 83 |
| 12 | -phenyl | 88 – 93 |
| 13 | -(4-chlorophenyl) | 110 – 111 |
| 14 | —CH₂-phenyl | 51 – 53 |

TABLE I-continued $$\underset{\underset{Cl}{\overset{Cl}{\bigvee}}}{\overset{O}{\overset{\|}{C}-S-R}}$$

| Compound No. | R | Physical Constant m.p. (° C) or $N_D^{30}$ |
|---|---|---|
| 15 | —CH$_2$—⟨benzene⟩—Cl | 94 – 95 |
| 16 | —CH$_2$—⟨benzene with Cl⟩—Cl | 101 – 104 |

As stated above the novel compounds of this invention exhibit plant growth regulatory activity. The compounds of this invention were tested as plant growth regulators in the following manner:

Plant Growth Regulatory Screening Test

A small Fiber flat, 7 inches × 5 inches × 2.5 inches, is filled with soil to a depth of 2 inches. Seeds of Pinto beans (*Phaseolus vulgaris*) are planted at a depth of 0.5 inch and covered with soil. Seeds are planted to give three seedlings per row. The flats are placed in a greenhouse at 70° to 85° F and watered daily with a sprinkler. About 8 to 12 days after planting when the primary leaves of the bean plants are almost fully expanded and the first trifoliate leaves are just starting to form, the plants are thinned to two plants per flat by cutting the excess weaker plants. Several days later the plants are sprayed with a solution of the test compound.

The solution is prepared by weighing out 20 mg of the test compound, dissolving it in 5 ml of acetone containing 1% Tween 20 ®, a polyoxyethylene sorbitan monolaurate, and then adding 5 ml of water. The solution is sprayed on the foliage using a No. 152 DeVilbiss atomizer at an air pressure of 5 lb/sq. in. The spray concentration is 0.2 and the rate is 8 lb/acre. The spray volume is 476 gal/acre. The treated plants are placed back in the greenhouse and care is taken to avoid sprinkling the treated foliage with water for three days after treatment. Plant growth regulatory effect is indicated by percent malformation (MF) and tip kill (TK) in Table II.

TABLE II

| Compound No. | Growth Regulation Effect |
|---|---|
| 1 | 80 MF |
| 2 | 80 TK |
| 3 | 80 MF |
| 4 | 80 MF |
| 5 | 80 MF |
| 6 | 80 MF |
| 7 | 80 MF |
| 8 | 80 MF |
| 9 | 80 MF |
| 10 | 80 MF |
| 11 | 80 MF |
| 12 | 80 MF |
| 13 | 80 MF |
| 14 | 80 MF |
| 15 | 80 MF |
| 16 | 80 MF |

Evaluation as Plant Growth Regulant on Soybeans

Dixie T5-09 plastic tubs with perforated bottoms were filled with a loamy sand soil. Five seeds of Bragg and Amsoy soybeans were planted 0.5 inches deep into the soil. The containers were placed in a greenhouse and the soil irrigated sufficiently to insure good germination and growth of the soybeans. Four weeks after planting the soybeans were thinned to one plant per tub. Test compounds were applied on a linear spray table. Desired application rates of 0.125, 0.25 and 0.5 lb/A ai were obtained by weighing 18.75, 37.5, and 75 mg ai of compound into 120 ml bottles, dissolving with 50 ml of acetone containing 1% Tween 20 ®, a polyoxyethylene sorbitan monolaurate, and diluting to 100 ml with water. After spraying the tubs were returned to a greenhouse and irrigated as needed without wetting the foliage for three days. Thereafter, standard irrigation procedures were followed. Six weeks after treatment the plants were rated visually. The degree of PGR activity was measured by percent stunting, apical inhibition, axillary branching, and leaf and bud proliferation. Phytotoxicity is indicated by leaf crinkle, leaf and pod malformation and small pod size. The number of soybean pods were also counted and recorded. Bragg soybean failed to produce pods due to greenhouse growing conditions. Results are shown in Table III were percent PGR = % Plant Growth Regulator activity/% Phytotoxicity.

TABLE III

| Compound No. | Rate (lb/A) | Bragg Soybean % PGR | Amsoy Soybean % PGR | Amsoy Soybean Pods/Plant |
|---|---|---|---|---|
| Untreated Plants | — | — | — | 33 |
| 1 | .125 | 0/0 | 0/0 | 30 |
|   | .25 | 10/0 | 20/0 | 40 |
|   | .50 | 25/0 | 30/0 | 44 |
| 2 | .125 | 10/0 | 20/0 | 32 |
|   | .25 | 10/0 | 30/20 | 35 |
|   | .50 | 30/10 | 40/30 | 40 |
| 3 | .125 | 0/0 | 0/0 | 32 |
|   | .25 | 0/0 | 10/0 | 44 |
|   | .50 | 0/0 | 20/0 | 37 |
| 4 | .125 | 0/0 | 0/0 | 32 |
|   | .25 | 0/0 | 10/0 | 28 |
|   | .50 | 20/0 | 20/0 | 37 |
| 5 | .125 | 0/0 | 10/0 | 30 |
|   | .25 | 20/0 | 20/0 | 37 |
|   | .50 | 40/0 | 30/0 | 33 |
| 6 | .125 | 0/0 | 10/0 | 24 |
|   | .25 | 10/0 | 25/0 | 37 |
|   | .50 | 25/0 | 40/20 | 42 |
| 7 | .125 | 10/0 | 10/0 | 31 |
|   | .25 | 25/0 | 20/0 | 31 |
|   | .50 | 40/0 | 25/10 | 33 |
| 8 | .125 | 20/0 | 25/10 | 25 |
|   | .25 | 40/20 | 50/20 | 34 |
|   | .50 | 50/40 | 50/40 | 22 |
| 9 | — | — | — | — |
|   | — | — | — | — |
|   | — | — | — | — |
| 10 | .125 | 0/0 | 10/0 | 37 |
|   | .25 | 20/0 | 20/0 | 27 |
|   | .50 | 20/10 | 20/30 | 33 |
| 11 | .125 | 0/0 | 0/0 | 33 |
|   | .25 | 20/10 | 10/10 | 25 |
|   | .50 | 20/20 | 25/0 | 36 |
| 12 | .125 | 0/0 | 0/0 | 40 |
|   | .25 | 20/10 | 0/0 | 33 |
|   | .50 | 20/20 | 0/0 | 29 |
| 13 | .125 | 0/0 | 0/0 | 32 |
|   | .25 | 20/10 | 10/0 | 30 |
|   | .50 | 20/20 | 30/0 | 33 |
| 14 | .125 | 20/10 | 0/0 | 34 |
|   | .25 | 20/10 | 0/0 | 26 |
|   | .50 | 20/20 | 20/0 | 24 |
| 15 | .125 | 0/0 | 0/0 | 26 |
|   | .25 | 0/0 | 0/0 | 37 |
|   | .50 | 20/10 | 20/0 | 32 |
| 16 | — | — | — | — |
|   | — | — | — | — |

TABLE III-continued

| Compound No. | Rate (lb/A) | Bragg Soybean % PGR | Amsoy Soybean % PGR | Pods/Plant |
|---|---|---|---|---|
| — | — | — | — | — |

As may be seen by the test results, the compounds of this invention are useful in regulating the growth habits of plants. Preferably the compounds are applied to the plant to be modified. It is necessary, of course, that the plants receive an effective or regulating amount, i.e., an amount sufficient to give the desired plant growth regulating effect. Since the amount of active agent required will vary to some extent, depending on the plant treated, precise limits on the amount employed can not be given. The tests set forth above indicated exemplary amounts which maybe used as will be readily appreciated by those skilled in the art. Determination of the optimum effective concentration for a specific application is readily conducted by routine procedures as will also be apparent to those skilled in the art.

The compounds are normally applied in the form of a composition alone or with a suitable carrier. Thus the compounds may be applied as a dust, spray, drench or aerosol. Suitable carriers include solvents, diluents, various surface agents, for example detergent, soaps or other emulsifying or wetting agents, surface active clays, carrier media, adhesives, spreading agents, humectants, and the like. They may also be combined with other biologically active compositions including fungicides, bactericides, algicides, insecticides, etc. as well as fertilizers, soil modifiers, etc. In general, depending on the carrier employed, the composition will contain up to about 75% of active ingredient.

What is claimed is:

1. A compound having the general structural formula

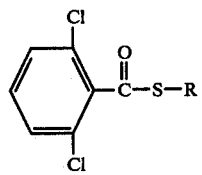

wherein R is selected from the group consisting of alkyl having 1-6 carbon atoms, cycloalkyl having 3-6 carbon atoms, cycloalkylmethyl wherein the cycloalkyl group has 3-6 carbon atoms, phenyl, substituted phenyl, and aralkyl having 7-10 carbon atoms.

2. The compound of claim 1 wherein R is n-propyl.
3. The compound of claim 1 wherein R is i-propyl.
4. The compound of claim 1 wherein R is methyl.
5. The compound of claim 1 wherein R is ethyl.
6. The compound of claim 1 wherein R is n-butyl.
7. The compound of claim 1 wherein R is i-butyl.
8. The compound of claim 1 wherein R is sec-butyl.
9. The compound of claim 1 wherein R is t-butyl.
10. The compound of claim 1 wherein R is cyclopropylmethyl.
11. The compound of claim 1 wherein R is neopentyl.
12. The compound of claim 1 wherein R is cyclohexyl.
13. The compound of claim 1 wherein R is phenyl.
14. The compound of claim 1 wherein R is 4-chlorophenyl.
15. The compound of claim 1 wherein R is benzyl.
16. The compound of claim 1 wherein R is 4-chlorobenzyl.
17. The compound of claim 1 wherein R is 3,4-dichlorobenzyl.
18. A plant growth regulatory composition comprising a plant growth regulatory effective amount of a compound having the general structural formula:

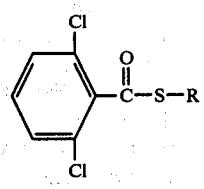

wherein R is selected from the group consisting of alkyl having 1-6 carbon atoms, cycloalkyl having 3-6 carbon atoms, cycloalkylmethyl wherein the cycloalkyl group has 3-6 carbon atoms, phenyl, substituted phenyl, and aralkyl having 7-10 carbon atoms.

19. The composition of claim 18 wherein the compound is n-propyl 2,6-dichlorothiolbenzoate.
20. The composition of claim 18 wherein the compound is i-propyl 2,6-dichlorothiolbenzoate.
21. The composition of claim 18 wherein the compound is methyl 2,6-dichlorothiolbenzoate.
22. The composition of claim 18 wherein the compound is ethyl 2,6-dichlorothiolbenzoate.
23. The composition of claim 18 wherein the compound is n-butyl 2,6-dichlorothiolbenzoate.
24. The composition of claim 18 wherein the compound is i-butyl 2,6-dichlorothiolbenzoate.
25. The composition of claim 18 wherein the compound is sec-butyl 2,6-dichlorothiolbenzoate.
26. The composition of claim 18 wherein the compound is t-butyl 2,6-dichlorothiolbenzoate.
27. The composition of claim 18 wherein the compound is cyclopropylmethyl 2,6-dichlorothiolbenzoate.
28. The composition of claim 18 wherein the compound is neopentyl 2,6-dichlorothiolbenzoate.
29. The composition of claim 18 wherein the compound is cyclohexyl 2,6-dichlorothiolbenzoate.
30. The composition of claim 18 wherein the compound is phenyl 2,6-dichlorothiolbenzoate.
31. The composition of claim 18 wherein the compound is 4-chlorophenyl 2,6-dichlorothiolbenzoate.
32. The composition of claim 18 wherein the compound is benzyl 2,6-dichlorothiolbenzoate.
33. The composition of claim 18 wherein the compound is 4-chlorobenzyl 2,6-dichlorothiolbenzoate.
34. The composition of claim 18 wherein the compound is 3,4-dichlorobenzyl 2,6-dichlorothiolbenzoate.
35. A method of regulating the growth of plants which comprises applying thereto an effective amount of a compound having the general structural formula:

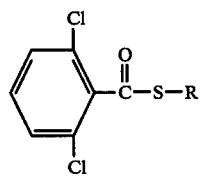

wherein R is selected from the group consisting of alkyl having 1-6 carbon atoms, cycloalkyl having 3-6 carbon atoms, cycloalkylmethyl wherein the cycloalkyl group has 3-6 carbon atoms, phenyl, substituted phenyl, and aralkyl having 7-10 carbon atoms.

36. The method of claim 35 wherein said compound is n-propyl 2,6-dichlorothiolbenzoate.

37. The method of claim 35 wherein said compound is i-propyl 2,6-dichlorothiolbenzoate.

38. The method of claim 35 wherein said compound is methyl 2,6-dichlorothiolbenzoate.

39. The method of claim 35 wherein said compound is ethyl 2,6-dichlorothiolbenzoate.

40. The method of claim 35 wherein said compound is n-butyl 2,6-diclorothiolbenzoate.

41. The method of claim 35 wherein said compound is i-butyl 2,6-dichlorothiolbenzoate.

42. The method of claim 35 wherein said compound is sec-butyl 2,6-dichlorothiolbenzoate.

43. The method of claim 35 wherein said compound is t-butyl 2,6-dichlorothiolbenzoate.

44. The method of claim 35 wherein said compound is neopentyl 2,6-dichlorothiolbenzoate.

45. The method of claim 35 wherein said compound is cyclopropylmethyl 2,6-dichlorothiolbenzoate.

46. The method of claim 35 wherein said compound is cyclohexyl 2,6-dichlorothiolbenzoate.

47. The method of claim 35 wherein said compound is phenyl 2,6-dichlorothiolbenzoate.

48. The method of claim 35 wherein said compound is 4-chlorophenyl 2,6-dichlorothiolbenzoate.

49. The method of claim 35 wherein said compound is benzyl 2,6-dichlorothiolbenzoate.

50. The method of claim 35 wherein said compound is 4-chlorobenzyl 2,6-dichlorothiolbenzoate.

51. The method of claim 35 wherein said compound is 3,4-dichlorobenzyl 2,6-dichlorothiolbenzoate.

52. The method of claim 35 wherein said compound is neopentyl 2,6-dichlorothiolbenzoate.

* * * * *